US006660293B2

(12) United States Patent
Giordano et al.

(10) Patent No.: US 6,660,293 B2
(45) Date of Patent: Dec. 9, 2003

(54) COMPOSITIONS AND METHODS FOR PROPHYLACTIC AND THERAPEUTIC SUPPLEMENTATION OF NUTRITION IN SUBJECTS

(75) Inventors: John A. Giordano, West Orange, NJ (US); Charles Balzer, Lavalette, NJ (US)

(73) Assignee: Everett Laboratories, Inc., West Orange, NJ (US)

( * ) Notice: Subject to any disclaimer, the term of this patent is extended or adjusted under 35 U.S.C. 154(b) by 0 days.

(21) Appl. No.: 09/982,205

(22) Filed: Oct. 19, 2001

(65) Prior Publication Data

US 2003/0012826 A1 Jan. 16, 2003

Related U.S. Application Data

(60) Provisional application No. 60/301,443, filed on Jun. 29, 2001.

(51) Int. Cl.$^7$ .............................................. A61K 47/00
(52) U.S. Cl. ..................... 424/439; 424/400; 424/451; 424/464; 424/489
(58) Field of Search ................ 424/400, 439, 424/451, 464, 489

(56) References Cited

U.S. PATENT DOCUMENTS

| | | | |
|---|---|---|---|
| 3,160,564 A | 12/1964 | Hanus | 167/81 |
| 4,710,387 A | 12/1987 | Uiterwaal et al. | 426/72 |
| 4,740,373 A | 4/1988 | Kesselman et al. | 424/141 |
| 4,804,535 A | 2/1989 | Kesselman et al. | 424/141 |
| 4,940,658 A | 7/1990 | Allen et al. | |
| 4,945,083 A | 7/1990 | Jansen, Jr. | 514/52 |
| 5,108,767 A | 4/1992 | Mulchandani et al. | 426/72 |
| 5,374,560 A | 12/1994 | Allen et al. | |
| 5,438,017 A | 8/1995 | Allen et al. | |
| 5,457,055 A | 10/1995 | Allen et al. | |
| 5,494,678 A | 2/1996 | Paradissis et al. | 424/439 |
| 5,514,382 A | 5/1996 | Sultenfuss | 424/440 |
| 5,556,644 A | 9/1996 | Chandra | 424/630 |
| 5,563,126 A | 10/1996 | Allen et al. | |
| 5,626,884 A | 5/1997 | Lockett | 424/639 |
| 5,795,873 A | 8/1998 | Allen | 514/52 |
| 5,869,084 A | 2/1999 | Paradissis et al. | 424/439 |
| 5,922,704 A | 7/1999 | Bland | 514/185 |
| 5,976,568 A | * 11/1999 | Riley | 424/451 |
| 6,042,849 A | 3/2000 | Richardson et al. | 424/682 |
| 6,048,846 A | 4/2000 | Cochran | |
| 6,090,414 A | 7/2000 | Passwater et al. | 424/702 |
| 6,103,756 A | * 8/2000 | Gorsek | 514/458 |
| 6,136,859 A | 10/2000 | Henriksen | 514/561 |
| 6,207,651 B1 | 3/2001 | Allen et al. | |
| 6,228,388 B1 | 5/2001 | Paradissis et al. | 424/439 |
| 6,245,360 B1 | 6/2001 | Markowitz | 424/641 |
| 6,255,341 B1 | 7/2001 | DeMichele et al. | 514/474 |
| 6,297,224 B1 | 10/2001 | Allen et al. | |
| 6,299,896 B1 | 10/2001 | Cooper et al. | 424/441 |
| 6,361,800 B1 | 3/2002 | Cooper et al. | 424/630 |
| 6,528,496 B1 | 3/2003 | Allen et al. | |
| 2001/0028896 A1 | 10/2001 | Byrd | 424/457 |
| 2001/0036500 A1 | 11/2001 | Uchida et al. | 426/590 |
| 2002/0015742 A1 | 2/2002 | Jackson et al. | 424/630 |
| 2002/0025310 A1 | 2/2002 | Bland | 424/94.1 |

FOREIGN PATENT DOCUMENTS

| | | |
|---|---|---|
| EP | 0 482 715 | 4/1992 |
| EP | 0 891 719 | 1/1999 |
| WO | 99/07419 | 2/1999 |

OTHER PUBLICATIONS

Stein et al., 3 Blood Purification 52–62 (1985).
Blumberg et al., 20(5) Clin. Nephrol. 244–50 (1983).
Allman et al., 150 Med. J. Australia 130–33 (1999).
Story et al., 27(1) Crit. Care Med. 220–23 (1999).
Makoff, 25 Miner. Electrolyte Metab. 349–51 (1999).
Shah et al., 18(1) Amer. J. Kidney Dis. 84–90 (1991).
Shah et al., 10(1) Amer. J. Kidney Dis. 42–49 (1992).
Vos, 161 Arch. Intern. Med. 774–75 (2001).
House et al., 45(1) ASAIO J. 94–97 (1999).
Descombes et al., 24(10) Artificial Organs 773–78 (2000).
The Vitatops Trial Study Group, 13 Cerebrovasc. Dis. 120–26 (2002).
Frank et al., 70(4) Int. J. Vitam. Nutr. Res. 159–66 (2000).
Dierkes et al., 11(2) J. Renal Nutr. 67–72 (2001).
Henning et al., 95(9) Medizin. Klinik 477–81 (2000).
Bazzarre et al., 12(2) J. Amer. Coll. Nutr. 162–69 (1993).
Gey, 52 Bibl. Nutr. Dieta. 75–91 (1995).
Chang et al., 51 Am. J. Clin. Nutr. 826–31 (1990).
Moser–Veillon et al., 52 Am. J. Clin. Nutr. 135–41 (1990).
Kang–Yoon et al., 56 Am. J. Clin. Nutr. 548–58 (1992).
Christian et al., 130(11) J. Nutr. 2675–82 (2000).
Kharb et al., 48(5) JAPI 484–485 (2000).
Agus et al., 17(1) Crit. Care Clin. 175–86 (2001).
Shechter et al., 102 Circulation 2353–2358 (2000).
Morris et al., 13 J. Trace Elements Med. Biol. 57–61 (1999).
Anderson, 26 Diabetes & Metabolism (Paris) 22–27 (2000).
Zacharski et al., 139(2) Amer. Heart J. 337–345 (2000).
Jaarsveld et al., 99(1) Res/ Comm. Mol. Pathol. Pharmacol. 69–80 (1998).
Lips et al., 86(3) J. Clin. Endocrin. Metab. 1212–1221 (2001).

(List continued on next page.)

*Primary Examiner*—Thurman K. Page
*Assistant Examiner*—Charesse Evans
(74) *Attorney, Agent, or Firm*—Preston Gates Ellis & Rouvelas Meeds LLP

(57) ABSTRACT

The present invention relates to compositions without added iron and methods for prophylactic nutritional supplementation and therapeutic nutritional supplementation. Specifically, the method involves administering to an individual a composition comprising carotenoids, vitamin E, vitamin D, vitamin C, thiamine, riboflavin, niacin, folic acid, pyridoxine, biotin, pantothenic acid, cobalamin, magnesium, manganese, zinc, selenium, chromium, copper, alpha lipoic acid, and lutein, wherein the composition is free of added iron.

84 Claims, No Drawings

OTHER PUBLICATIONS

Dawson–Hughes et al., 337(10) New Eng. J. Med. 670–676 (1997).
Cattaneo, 32(Supp 1) Ann. Med. 46–52 (2000).
Maxwell, 95(Supp 1) Basic Res. Cardiol. 66–71 (2000).
Hanratty et al., 85 Heart 326–330 (2001).
Schlaich et al., 153 Atherosclerosis 383–389 (2000).
Haak et al., 108 Exp. Clin. Endocrinol. Diab. 168–174 (2000).
Rudich et al., 42 Diabetologia 949–957 (1999).
Kagan et al., 44(8) Biochem. Pharmacol. 1657–1649 (1992).
Bernstein et al., 72 Exp. Eye Res. 215–223 (2001).
Mares–Perlman et al., 153(5) Amer. J. Epidemiol. 424–432 (2001).
Mayne, 10 FASEB J. 690–701 (1996).
Omenn et al., 334(18) New Eng. J. Med. 1150–1155 (1996).
Holben et al., 99(7) J. Amer. Diet. Assoc. 836–843 (1999).
Carr et al., 87 Circ. Res. 349–354 (2000).
Porkkala–Sarataho et al., 20 Arterioscler. Thromb. Vasc. Biol. 2087–2093 (2000).
Esterbauer et al., 13 Free Rad. Biol. Med. 341–390 (1992).
Haberland et al., 113(2) Amer. Heart J. 573–577 (1987).
Henriksen et al., 3(2) Arteriosclerosis 149–159 (1983).
Rapp et al., 41 Invest. Ophthalmol. Vis. Sci. 1200–1209 (2000).
Rock et al., 96(7) J. Amer. Diet. Assoc. 693–702 (1996).
Berendschot et al., 41 Invest. Ophthalmol. Vis. Sci. 3322–3326 (2000).
Cousins, Present Knowledge In Nutrition 293–306 (Ziegler et al., eds., 7$^{th}$ ed. ILSI Press) (1996).
Burton et al., Ann. NY Acad. Sci. 7–22 (1998).
Anderson et al., 54 Amer. J. Clin. Nutr. 909–916 (1991).
Islam et al., 150 Atherosclerosis 217–224 (2000).
Hoogeveen et al., 101 Circulation 1506–1511 (2000).
Kishi et al., 48 Diabetes 2045–2051 (1999).
Heller et al., 276 J. Biol. Chem. 40–47 (2001).
Huang et al., 275(23) J. Biol. Chem. 17399–17406 (2000).
Vincent, 130 J. Nutr. 715–718 (2000).
Fraker et al., 130 J. Nutr. 1399S–1406S (2000).
Uauy et al., 67 Amer. J. Clin. Nutr. 952S–959S (1998).
Shankar et al., 68 Amer. J. Clin. Nutr. 447S–463S (1998).
Stampfer et al., 328 New Eng. J. Med. 1444–49 (1993).
Burk, 3 Ann. Rev. Nutrition 53–70 (1983).
Henkin et al., 91 Am. J. Med. 239–46 (1991).
Bostom et al., 49 Kidney Int. 147–52 (1996).
Robinson et al., 94 Circulation 2743–48 (1996).
Braguer et al., 57 Nephron 192–96 (1991).
Shecter et al., 102 Circulation 2353–58 (2000).
Zima et al., 17 Blood Purif. 182–86 (1999).
Weigel et al., 12 Cont. Clin. Trials 378–94 (1991).

\* cited by examiner

COMPOSITIONS AND METHODS FOR PROPHYLACTIC AND THERAPEUTIC SUPPLEMENTATION OF NUTRITION IN SUBJECTS

CROSS REFERENCE TO RELATED APPLICATION

The present invention is related to and, in accordance with the provisions of 35 U.S.C. §119(e), claims the benefit of provisional patent application Serial No. 60/301,443 filed Jun. 29, 2001, which is expressly incorporated fully herein by reference.

FIELD OF THE INVENTION

The present invention relates to compositions comprising various vitamins and minerals, and without added iron, and methods for using these compositions for prophylactic nutritional supplementation and therapeutic nutritional supplementation in, for example, physiologically stressful conditions and to minimize the effect of exogenous iron supplementation.

BACKGROUND OF THE INVENTION

Nutrition plays a critical role in maintaining good health. Proper nutrition prevents dietary deficiencies, and also protects against the development of disease. Proper nutrition plays an increasingly important role as the body faces physiological stress. For example, as the body ages it suffers significant physiological stresses. Specifically, as the body metabolism shifts to accumulating larger fat stores and decreasing lean body mass, this increase in body weight may lead to obesity and associated conditions such as diabetes, cardiovascular disease, hypertension, osteoarthritis, and cancer. Other conditions, such as anorexia, malnutrition, gastrointestinal disorders, chronic alcoholism, chronic infections, acute infections, congestive heart failure, hyperthyroidism, poorly controlled diabetes, cheilosis, gingivitis, stomatitis and dietary restrictions, often result in physiological stresses that may be exacerbated by poor nutrition. In particular, these disease states may result in increased oxidative stress or elevated homocysteine levels that further compromise health.

Thus, nutritional supplementation serves a vital role in protecting against poor nutrition and disease. More specifically, nutritional supplementation may provide the necessary vitamins, minerals, and other nutrients that might otherwise be lacking in the diet, and provide the nutritional defense against disease development. The invention herein provides for compositions and methods, specifically using an iron-free multi-vitamin/mineral/antioxidant formulation, designed to optimize health and wellness, minimize oxidative stress, and normalize homocysteine levels.

SUMMARY OF THE INVENTION

The present invention provides nutritional compositions without iron and methods of using these compositions for both prophylactic and therapeutic nutritional supplementation, specifically in physiologically stressful conditions. Specifically, the present invention relates to novel compositions of vitamins and minerals, without exogenous iron, that can be used to supplement the nutritional deficiencies observed in patients with anorexia, malnutrition, gastrointestinal disorders, chronic alcoholism, chronic infections, acute infections, congestive heart failure, hyperthyroidism, poorly controlled diabetes, cheilosis, gingivitis, stomatitis, and/or dietary restrictions. In addition, the compositions may be used to treat the nutritional deficiencies of patients suffering from a disease state that results in increased oxidative stress or elevated homocysteine levels.

The compositions of the present invention include various vitamins and minerals that improve the nutritional state of a patient; these compositions preferably may be used therapeutically or prophylacticly. The vitamins of the present invention may preferably comprise one or more of carotenoids, vitamin E, vitamin $D_3$, vitamin C, thiamine, riboflavin, niacin, folic acid, pyridoxine, biotin, pantothenic acid, and cyanocobalamin. The minerals of the present invention may preferably include one or more of magnesium, manganese, zinc, selenium, chromium, and copper. In addition, the present invention may preferably comprise other nutritional elements, such as alpha lipoic acid, and/or lutein. The compositions of the present invention preferably do not include exogenous iron as an added component.

In a preferred embodiment, the compositions of the present invention comprise carotenoids in a range of about 2400 IU to about 3600 IU, vitamin E in a range of about 80 IU to 120 IU, vitamin D in a range of about 320 IU to about 480 IU, vitamin C in a range of about 240 mg to 360 mg, thiamine in a range of about 16 mg to 24 mg, riboflavin in a range of about 4 mg to about 6 mg, niacin in a range of about 20 mg to about 30 mg, folic acid in a range of about 0.8 mg to 1 mg, pyridoxine provided in a range of about 20 mg to 30 mg, biotin in a range of about 80 µg to about 120 µg, pantothenic acid in a range of about 12 mg to about 18 mg, cobalamin in a range of about 40 µg to about 60 µg, magnesium in a range of about 40 mg to about 60 mg, manganese in a range of about 1.2 mg to about 1.8 mg, zinc in a range of about 20 mg to about 30 mg, selenium in a range of about 80 µg to 120 µg, chromium in a range of about 40 µg to about 60 µg, copper in a range of about 1.2 mg to about 1.8 mg copper, lipoic acid in a range of about 12 mg to about 18 mg, and lutein in a range from about 4 mg to 6 mg, wherein these compositions are free of added iron.

In another embodiment of the compositions of the present invention, vitamin E is present as d-alpha tocopheryl succinate, vitamin D is vitamin $D_3$, niacin is niacinamide, chromium is chromium chloride, selenium is present as sodium selenate, zinc is zinc oxide, carotenoids consist of alpha-carotene, beta-carotene, cryptoxanthin, lutein and zeaxanthin, magnesium is magnesium oxide, manganese is present as manganese sulfate, and copper is cupric sulfate.

In a further preferred embodiment of the present invention, the composition includes about 3000 IU carotenoids, about 100 IU d-alpha tocopheryl succinate, about 400 IU vitamin $D_3$, about 300 mg vitamin C, about 20 mg thiamine, about 5 mg riboflavin, about 25 mg niacinamide, about 1.0 mg folic acid, about 25 mg pyridoxine HCl, about 100 µg biotin, about 15 mg calcium pantothenate, about 50 µg cyanocobalamin, about 50 mg magnesium oxide, about 1.5 mg manganese sulfate, about 25 mg zinc oxide, about 100 µg selenium, about 50 µg chromium chloride, about 1.5 mg cupric sulfate, about 15 mg alpha lipoic acid, and about 5 mg lutein, wherein this composition is free of added iron.

In addition, the compositions of the present invention may be administered to an individual on a daily basis and the composition may be administered orally. Furthermore, the compositions of the present invention may include a pharmaceutically acceptable carrier.

The present invention also relates to methods for supplementing nutritional deficiencies in a patient or person by administering a composition comprising carotenoids, vitamin E, vitamin D, vitamin C, thiamine, riboflavin, niacin, folic acid, pyridoxine, biotin, pantothenic acid, cobalamin, magnesium, manganese, zinc, selenium, chromium, copper, alpha lipoic acid, and lutein, wherein this composition is free of added iron.

The methods of the present invention may be used to treat patients suffering from anorexia, malnutrition, gastrointestinal disorders, chronic alcoholism, chronic infections, acute infections, congestive heart failure, hyperthyroidism, poorly controlled diabetes, cheilosis, gingivitis, stomatitis, and dietary restrictions. In addition, these methods may be used to treat the nutritional deficiencies in patients suffering from a disease state that results in increased oxidative stress or elevated homocysteine levels.

In a preferred embodiment, the methods of the present invention utilize compositions comprising carotenoids in a range of about 2400 IU to about 3600 IU, vitamin E in a range of about 80 IU to about 120 IU, vitamin D in a range of about 320 IU to about 480 IU, vitamin C in a range of about 240 mg to 360 mg, thiamine in a range of about 16 mg to about 24 mg, riboflavin in a range of about 4 mg to about 6 mg, niacin in a range of about 20 mg to about 30 mg, folic acid in a range of about 0.8 mg to about 1 mg, pyridoxine provided in a range of about 20 mg to about 30 mg, biotin in a range of about 80 µg to about 120 µg, pantothenic acid in a range of about 12 mg to about 18 mg, cobalamin in a range of about 40 µg to about 60 µg, magnesium in a range of about 40 mg to about 60 mg, manganese in a range of about 1.2 mg to about 1.8 mg, zinc in a range of about 20 mg to about 30 mg, selenium in a range of about 80 µg to about 120 µg, chromium in a range of about 40 µg to about 60 µg, copper in a range of about 1.2 mg to about 1.8 mg copper, lipoic acid in a range of about 12 mg to about 18 mg, and lutein in a range from about 4 mg to about 6 mg, wherein these compositions are free of added iron.

In a further preferred embodiment, the methods of the present invention utilize a composition comprising about 3000 IU carotenoids, about 100 IU d-alpha tocopheryl succinate, about 400 IU vitamin $D_3$, about 300 mg vitamin C, about 20 mg thiamine, about 5 mg riboflavin, about 25 mg niacinamide, about 1.0 mg folic acid, about 25 mg pyridoxine HCl, about 100 µg biotin, about 15 mg calcium pantothenate, about 50 µg cyanocobalamin, about 50 mg magnesium oxide, about 1.5 mg manganese sulfate, about 25 mg zinc oxide, about 100 µg selenium, about 50 µg chromium chloride, about 1.5 mg cupric sulfate, about 15 mg alpha lipoic acid, and about 5 mg lutein, wherein this composition is free of added iron.

DETAILED DESCRIPTION

Proper nutrition is essential for maintaining health and preventing diseases. The compositions and methods of the present invention provide the means to optimize good health by utilizing vitamin, mineral, and antioxidant nutritional supplementation. More specifically, the compositions of the present invention contain a variety of antioxidants, which may minimize free radical concentrations and minimize the deleterious effects of oxidative stress, and vitamins and minerals that support normal levels of homocysteine. It is to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise.

The compositions of the present invention may preferably comprise antioxidant factors that may protect against oxidative stress. Oxidative stress occurs as the body's natural use of oxygen creates unstable molecules known as free radicals, which steal stable electron partners from other molecules, launching more free radicals and increased molecular and cellular instability. This 'oxidative stress' is implicated in over 200 diseases, including cardiovascular disease and cancer, which are attributed to free radical oxidation. Rock et al., 96 J. AM. DIETARY ASSOC. 693–702 (1996). For example, lipid peroxidation is the initiating step in the oxidation of low-density lipoproteins (LDL). In turn, the lipid peroxides oxidize other lipoproteins, which are taken up by the cells of the arterial wall. Eventually, the deposited oxidized lipoproteins form an atherosclerotic plaque. Id. The antioxidant components of the compositions and methods described herein may preferably include one or more of vitamin E, selenium, vitamin C, carotenoids, lutein, and lipoic acid.

The compositions and methods of the present invention also may preferably include B-complex vitamins, which are critical for health as each is part of one or more coenzymes in metabolizing food properly. This class of vitamins is water-soluble nutrients, not stored significantly in the body. Importantly, the B-complex vitamins may help normalize homocysteine levels and metabolism. High homocysteine levels have been correlated directly with increased risk of atherosclerosis and other heart disease. Although the exact mechanism by which homocysteine contributes to heart disease is not fully understood, it may act as an endothelial irritant that promotes atherosclerosis by inducing endothelial dysfunction. B-complex vitamins are required for the proper function of the homocysteine metabolic pathway, thus maintaining adequate levels of these vitamins may assist in normalizing homocysteine levels and maintaining good health. The B-complex vitamins of the present compositions and methods may preferably include one or more of thiamin ($B_1$), riboflavin ($B_2$), niacin ($B_3$), pantothenic acid, biotin, folic acid, pyridoxine ($B_6$) and cobalamin ($B_{12}$).

Minerals are inorganic, or non-carbon-containing, elements that are critical for healthy physiological processes, and are contemplated in the compositions and methods of the present invention. For example, minerals act as cofactors for hundreds of enzymes that range from those associated, for example, with food digestion, nucleic acid production, protein synthesis to antioxidant enzymes. One particular mineral, chromium, is essential in healthy insulin function, as it plays a direct role in insulin's interactions at the cellular level. The minerals of the compositions and methods of the present invention may preferably include one or more of chromium, zinc, copper, magnesium, and manganese.

Another mineral, iron, is specifically excluded from the compositions and methods of the present invention. Although iron is an essential mineral with many functions, iron has also been implicated as a catalyst for lipid oxidation. Specifically, lipid oxidation associated with LDL cholesterol has been correlated strongly with an increased risk of cardiovascular disease. Moreover, some older patients exhibit sensitivity to iron or build-up of iron concentration in the liver. Although iron supplementation may be indicated in specific population groups or disease states, universal supplementation may not always be recommended. Hence, the compositions and methods of the present invention are preferably free of added iron.

Vitamin D may preferably be a component of the compositions and methods of the present invention. Vitamin D is a fat-soluble "hormone like" substance essential for healthy bones. This vitamin increases the absorption of calcium and phosphorous from the gastrointestinal tract, and improves essential mineral resorption into bone tissue. Vitamin D can be converted to its active form from exposure of the skin to sunlight. This fact is among the reasons why vitamin D deficiency is common in the elderly, notably the institutionalized, who spend little or no time out of doors. Deficiencies lead to increased bone turnover and loss, and when severe, osteomalacia or softening of the bones. Supplementation with vitamin D has been shown to moderately reduce bone loss, increase serum 25-hydroxyvitamin D, and decrease serum parathyroid hormone levels. Dawson-Hughes et al., 337 NEW ENG. J. MED. 670–76 (1997); Lips et al., 86 J. CLIN. ENDOCRINOL. METAB. 1212–21 (2001).

Preferably, the vitamin D of the compositions and methods of the present invention is vitamin $D_3$. In the body, vitamin $D_3$ is produced when its precursor is exposed to ultraviolet irradiation (e.g., sunlight) and then hydroxylated in the liver to form 25-hydroxyvitamin $D_3$, the major form of vitamin D in the circulation. This form of the vitamin may be hydroxylated again in the kidney, yielding 1,25 hydroxyvitamin $D_3$, the most potent form of vitamin D. As noted above, vitamin $D_3$ plays a role in the maintenance of calcium and phosphorus homeostasis, but it is also active in cell differentiation and immune function. In a preferred embodiment of the invention, vitamin $D_3$ is present in the amount ranging from about 320 IU to about 480 IU. In a particularly preferred embodiment, vitamin $D_3$ is present in an amount of about 400 IU.

As discussed previously, the antioxidant components of the compositions and methods described herein preferably include vitamin E, selenium, vitamin C, carotenoids, lutein, and lipoic acid.

Vitamin E is a fat-soluble vitamin antioxidant found in biological membranes where it protects the phospholipid membrane from oxidative stress. More specifically, alpha-tocopherol, the most abundant and most active form of the vitamin E family, is the principle lipid-soluble, chain breaking antioxidant in tissue and plasma. RECOMMENDED DIETARY ALLOWANCES 99–101 (Nat'l Research Council, 10th ed., 1989) (hereinafter "RDA"). Vitamin E inhibits the oxidation of unsaturated fatty acids by trapping peroxyl free radicals. It is also an antiatherogenic agent, and studies have demonstrated a reduced risk of coronary heart disease with increased intake of vitamin E. Stampfer et al., 328 New Eng. J. MED. 1444–49 (1993). Vitamin E is available in various forms known to those of skill in the art. In a preferred embodiment of the present invention, vitamin E is present in an amount ranging from about 80 IU to about 120 IU. In a particularly preferred embodiment of the invention, vitamin E is present d-alpha tocopheryl succinate. A preferred embodiment of the invention includes about 100 IU d-alpha tocopheryl succinate.

Along with vitamin E, the mineral selenium is a component of the antioxidant enzyme, glutathione peroxidase, which plays a critical role in the control of oxygen metabolism, particularly catalyzing the breakdown of hydrogen peroxide. Burk, 3 ANN. REV. NUTRITION 53–70 (1983). Glutathione peroxidase prevents the generation of free radicals and decreases the risk of oxidative damage to numerous tissues, including the vascular system. Holben, 99 J. AM. DIETARY Assoc. 836–43 (1999). Another selenoprotein is the enzyme iodothyronine 5'-diodinase that converts thyroxine ($T_4$) to triiodothyronine ($T_3$). Selenium is available in many forms known to those of ordinary skill in the art. In a preferred embodiment of the present invention, selenium is included in a range of about 80 $\mu$g to about 120 $\mu$g. In a preferred embodiment of the invention, selenium is present as sodium selenate. A preferred embodiment of the invention includes about 100 $\mu$g sodium selenate.

Vitamin C (also known as ascorbic acid) is another antioxidant present in the invention described herein. The major biochemical role of the water-soluble vitamin C is as a co-substrate in metal catalyzed hydroxylations, and it has antioxidant properties in interacting directly with superoxide hydroxyl radicals and singlet oxygen. Vitamin C also provides antioxidant protection for folate and vitamin E, keeping vitamin E in its most potent form. It also enhances the absorption of iron. RDA, at 115. In addition, vitamin C is required for collagen synthesis, epinephrine synthesis, and bile acid formation. Moreover, vitamin C has been implicated in inhibiting atherosclerosis by being present in extracellular fluid of the arterial wall and potentiating nitric oxide activity, thus normalizing vascular function. A preferred embodiment of the compositions of the present invention includes a supplemental dose of vitamin C, preferably in the amount of about 240 mg to about 360 mg. A preferred embodiment of the present invention includes about 300 mg of vitamin C.

Along with vitamins E and C, and selenium, carotenoids are a group of antioxidants embodied in the present invention. There are over 600 carotenoids occurring naturally in fruits and vegetables. Many of these fat-soluble compounds, of which beta-carotene is a well-known example, have pro-vitamin A activity as well as antioxidant activity. Less-known carotenoids include alpha-carotene, lutein, cryptoxanthine, and zeaxanthin. The compositions and methods herein include a cartonoid complex that closely mirrors that found naturally in fruits and vegetables. In particular, the carotenoids of the present invention may preferably include alpha-carotene, beta-carotene, cryptoxanthin, lutein, and zeaxanthin. In particular, lutein and zeaxanthin are the major carotenoids that make up the macular pigment of the eye's retina, and their antioxidant properties protect the eye from light-induced damage and macular degeneration. Berendschot et al., 41 INVEST. OPHTHALMOL. VIS. SCI. 3322–26 (2000). In a preferred embodiment of the invention, carotenoids are included in a range of about 2400 IU to about 3600 IU. In a more preferred embodiment of the invention, the carotenoids include a mixture of alpha-carotene, beta-carotene, cryptoxanthin, lutein, and zeaxanthin. A preferred embodiment of the invention includes about 3000 IU of a mixture of alpha-carotene, beta-carotene, cryptoxanthin, lutein, and zeaxanthin.

Lutein is also preferably included in the compositions and methods described herein and is preferably included in an amount distinguished from that included in the mixed carotenoids. Regarding the antioxidant activity of lutein, scientists have demonstrated that lutein is an effective antioxidant capable of scavenging peroxyl radicals and quenching reactive oxygen species. Rapp et al., 41 INVEST. OPHTHALMOL. VIS. SCI. 1200–09 (2000). Thus, the compositions and methods of the present invention may include lutein, preferably in the amount ranging from about 4 mg to about 6 mg. A preferred embodiment of the invention comprise about 5 mg lutein.

Lipoic acid is an antioxidant and is preferably included in the compositions and methods of the present invention. Known as the "universal antioxidant," alpha lipoic acid is both a lipid- and water-soluble antioxidant that works synergistically with other antioxidants in the cell's mitochondria. In addition to working with other antioxidant nutrients, lipoic acid has powerful, pro-antioxidant enzyme properties. Alpha lipoic acid is also a cofactor for several regulatory enzymes, including pyruvate dehydrogenase, and appears to have an effect on glucose transport and utilization. Rudich et al., 42 DIABETOLOGIA 949–57 (1999). Alpha lipoic acid also increases tocopherol activity and acts as a metal chelator. Furthermore, alpha lipoic acid improves microvascular perfusion. Haak et al., 108 EXPERIMENTAL & CLINICAL ENDOCRINOLOGY & DIABETES 168–74 (2000). A preferred embodiment of the compositions of the present invention comprises alpha lipoic acid in the amount ranging from about 12 mg to about 18 mg. A particularly preferred embodiment of the present invention comprises about 15 mg of lipoic acid.

In addition to antioxidants, the compositions and methods of the present invention also preferably include one or more B-complex vitamins such as thiamin ($B_1$), riboflavin ($B_2$), niacin ($B_3$), pantothenic acid ($B_5$), biotin, folic acid, pyridoxine ($B_6$) and cobalamin ($B_{12}$).

Thiamine (vitamin $B_1$) plays a role in carbohydrate metabolism and neural function. It is a coenzyme for the oxidative decarboxylation of alpha-ketoacids (e.g., alpha-ketoglutarate and pyruvate) and for transketolase which is a component of the pentose phosphate pathway. Folate deficiency and malnutrition inhibit the activity of thiamine. RDA, at 123. One embodiment of the compositions of the present invention may comprise thiamine, preferably in the amount ranging from about 16 mg to about 24 mg. In a preferred embodiment of the present invention, the form of thiamine is thiamine HCl. A preferred embodiment of the invention comprises about 20 mg thiamine HCl.

Riboflavin (vitamin $B_2$) is a component of two flavin coenzymes, flavin mononucleotide (FMN) and flavin adenine dinucleotide (FAD). These flavoenzymes are involved in a number of oxidation-reduction reactions including the conversion of pyridoxine and niacin. RDA, at 132. Flavoenzymes also play a role in a number of metabolic pathways such as citric acid cycle, amino acid deamination, purine degradation, and fatty acid oxidation and thus help to maintain carbohydrate, amino acid, and lipid metabolism. In one embodiment, the compositions and methods of the present invention comprise riboflavin, preferably in the amount ranging from about 4 mg to about 6 mg. A preferred embodiment of the invention comprises about 5 mg of riboflavin.

Niacin, also called vitamin $B_3$, is the common name for two compounds: nicotinic acid (also called niacin) and niacinamide (also called nicotinamide). Niacin and is particularly important for maintaining healthy levels and types of fatty acids. Niacin is also required for the synthesis of pyroxidine, riboflavin, and folic acid. RDA, at 137. Administration of niacin may also produce a reduction in total cholesterol, LDL, and very low density lipoprotein (VLDL) levels; and an increase in high density lipoprotein (HDL) cholesterol levels. Nicotinamide adenine dinucleotide (NAD) and NAD phosphate (NADP) are active coenzymes of niacin. These coenzymes are involved in numerous enzymatic reactions such as glycolysis, fatty acid metabolism, and steroid synthesis. Henkin et al., 91 AM. J. MED. 239–46 (1991). One embodiment of the compositions and methods of the present invention may comprise niacin, preferably in the amount ranging from about 20 mg to about 30 mg. In a preferred embodiment of the invention, niacin is present in the form of niacinamide. A preferred embodiment of the invention comprises about 25 mg of niacinamide.

Folic acid (vitamin $B_8$), also called folate or methylfolate, is essential for the formation of red and white blood cells within bone marrow and also plays a role in heme formation. RDA, at 150. Folic acid in its active form, tetrahydrofolate, is a coenzyme that is involved in the transfer of methyl groups and it plays a role in DNA synthesis, purine synthesis, and amino acid synthesis, such as the conversion of glycine to serine and the transformation of homocysteine to methionine. The activation of folic acid requires a vitamin $B_{12}$-dependent transmethylation and vitamin $B_{12}$ is also necessary for folic acid delivery to tissues. Id. One embodiment of the compositions and methods of the present invention may comprise folic acid, preferably in the amount ranging from about 0.8 mg to about 1.0 mg. A preferred embodiment of the invention comprises about 1 mg of folic acid.

Pyridoxine (vitamin $B_6$) is another B-complex vitamin included in the compositions and methods described herein. The administration of pyridoxine may reduce the levels of homocysteine. Bostom et al., 49 KIDNEY INT. 147–52 (1996). The active forms of pyridoxine, pyridoxal-5'-phosphate (PLP) and pyridoxamine-5'-phosphate, are coenzymes for numerous enzymes and as such, are essential for gluconeogenesis, niacin formation, and erythrocyte metabolism. RDA, at 142–143. Pyridoxine is a coenzyme for both cystathionine synthase and cystathionase, enzymes that catalyze the formation of cysteine from methionine. Homocysteine is an intermediate in this process and elevated levels of plasma homocysteine are recognized as a risk factor for vascular disease. Robinson et al., 94 CIRCULATION 2743–48 (1996). Hence, one embodiment of the compositions and methods of the present invention may comprise pyridoxine, preferably in the amount ranging from about 20 mg to about 30 mg. In a preferred embodiment of the invention, pyridoxine is in the form of pyridoxine HCl. A preferred embodiment of the invention comprises about 25 mg pyridoxine HCl.

Biotin, another water-soluble B-complex vitamin, acts a coenzyme for a number of carboxylases, and thus has an important role in gluconeogenesis, fatty acid metabolism, and amino acid metabolism. RDA, at 166. For example, biotin serves as a carboxyl carrier for pyruvate carboxylase, which is involved in gluconeogenesis; acetyl CoA carboxylase, which is involved in fatty acid synthesis; and propionyl-CoA carboxylase, which is involved in glucose production. Researchers believe that biotin inhibits the effects of uremic toxins on tubulin polymerizaton. Braguer et al., 57 NEPHRON 192–96 (1991). Thus, one embodiment of the compositions and methods of the present invention comprises biotin, preferably in the amount ranging from about 80 $\mu$g to about 120 $\mu$g. A preferred embodiment of the invention comprises about 100 $\mu$g biotin.

Pantothenic acid (vitamin $B_5$) is a component of both the coenzyme A macromolecule and the acyl-carrier protein. These coenzymes function as carriers for acyl groups and are required for the synthesis of fatty acids, cholesterol, steroid hormones, and neurotransmitters. The coenzyme A complex also has a major role in the acetylation and acylation of numerous proteins. RDA, at 169. One embodiment of the compositions and methods of the present invention comprises pantothenic acid, preferably in the amount ranging from about 12 mg to about 18 mg. In a preferred embodiment of the invention, pantothenic acid is present as calcium pantothenate. A preferred embodiment of the invention comprises about 15 mg calcium pantothenate.

Cobalamin (vitamin $B_{12}$), another important vitamin included in the compositions and methods described herein, can be converted to the active coenzymes, methylcobalamin and 5'-deoxyadenosylcobalamin. These coenzymes are necessary for folic acid metabolism, conversion of coenzyme A, and myelin synthesis. For example, methylcobalamin catalyzes the demethylation of a folate cofactor, which is involved in DNA synthesis. A lack of demethylation may result in folic acid deficiency. RDA, at 159–160. Deoxyadenosylcobalamin is the coenzyme for the conversion of methylmalonyl-CoA to succinyl-CoA, which plays a role in the citric acid cycle. Importantly, cobalamin, along with pyridoxine and folic acid in implicated in the proper metabolism of homocysteine. Cobalamin is available as cyanocobalamin, methylcobalamin, hydroxocobalamin, adenosylcobalamin, and hydroxycyanocobalamin. One embodiment of the compositions and methods of the present invention may comprise cobalamin, preferably in the amount ranging from about 40 µg to about 60 µg. In a preferred embodiment of the invention, cobalamin is present as cyanocobalamin. A preferred embodiment of the invention includes about 50 µg cyanocobalamin.

As noted previously, minerals are inorganic elements that play a crucial role in physiological processes in the body relating to good health. The compositions and methods of the present invention may comprise minerals, and, in a preferred embodiment, comprise one or more of selenium, discussed above, and magnesium, manganese, zinc, chromium, and copper.

Magnesium is found primarily in both bone and muscle. Magnesium is an essential component for over 300 enzymes, including enzymes of biosynthetic pathways, glycolysis, protein synthesis, transketolase reactions, and membrane transport. Magnesium is also involved in the formation of cAMP, a cytosolic second messenger that plays a role in cell signaling mechanisms. In addition, magnesium functions both synergistically and antagonistically with calcium in neuromuscular transmission. RDA, at 188. Specifically, magnesium is critical for the maintenance of electrochemical potentials of nerve and muscle membranes and the neuromuscular junction transmissions, particularly important in the heart. Not surprisingly, magnesium deficiency is tied to cardiovascular disease and hypertension. Agus et al., 17 CRIT. CARE CLINICS 175–87 (2001). Indeed, oral magnesium therapy improves endothelial function in patients with coronary disease. Shechter et al., 102 CIRCULATION 2353–58 (2000). Yet, most individuals in the U.S. receive only about seventy-five percent of the magnesium they need from their diets. Magnesium is available in a variety of salts. One embodiment of the compositions and methods of the present invention comprises magnesium, preferably in the amount ranging from about 40 mg to about 60 mg. In a preferred embodiment of the invention, magnesium is present as magnesium oxide. A preferred embodiment of the invention comprises about 50 mg magnesium oxide.

Manganese, like magnesium, plays a key role in multiple enzymes and is needed for healthy skin, bone, and cartilage formation, as well as glucose tolerance. For example, manganese is a cofactor for enzymes such as glutamine synthetase, pyruvate carboxylase, and mitochrondrial superoxide dismutase. RDA, at 230. In particular, manganese is essential for glycoprotein and proteoglycan synthesis, and thus is involved in the formation of connective and skeletal tissue, as well as carbohydrate and lipid metabolism. It also helps activate superoxide dismutase, an important antioxidant enzyme. Manganese is available in many forms known to those of ordinary skill in the art, including manganese sulfate, manganese oxide, manganese oxy-sulfate, and manganese proteinate. One embodiment of the compositions and methods of the present invention comprises manganese, preferably in the amount ranging from about 1.2 mg to about 1.8 mg. In a preferred embodiment, manganese is present as manganese sulfate. A preferred embodiment of the invention comprises about 1.5 mg of manganese sulfate.

Zinc plays a role in numerous metabolic activities such as nucleic acid production, protein synthesis, and development of the immune system. There are more than 200 zinc metalloenzymes including aldolase, alcohol dehydrogenase, RNA polymerase, and protein kinase C. Zima et al., 17 BLOOD PURIF. 182–86 (1999). Moreover, zinc stabilizes RNA and DNA structures, forms zinc fingers in nuclear receptors, and is a component of chromatin proteins involved in transcription and replication. Zinc is available in many forms, such as zinc oxide and zinc sulfate. One embodiment of the compositions and methods of the present invention comprises zinc, preferably in the amount ranging from about 20 mg to about 30 mg. More preferably, zinc may be present as zinc oxide. A preferred embodiment of the invention comprises about 25 mg zinc oxide.

The trace mineral chromium harmonizes with insulin at the cellular level to optimize the release of energy from glucose, as well as maintaining proper cellular lipid or fat metabolism. Specifically, chromium increases insulin binding to cells, insulin receptor number, and activates the insulin receptor kinase leading to increased insulin sensitivity. Several studies suggest that adequate chromium levels are needed for optimal glycemic control. See, e.g., Anderson et al., 26 DIABETES METABOLABOLISM 22–27 (2000); Vincent, 130 J. NUTRITION 715–18 (2000). The concentration of chromium declines with age, and coronary artery disease appears to be associated with low levels of chromium. RDA, at 241. Yet, ninety percent of adults in the U.S. consume less than the recommended minimum amount of chromium. Chromium is available in various forms known to those skilled in the art, such as chromium chloride, chromium sulfate, chromium potassium sulfate, and chromium picolinate. One embodiment of the compositions and methods of the present invention comprises chromium, preferably in the amount ranging from about 40 µg to about 60 µg. Preferably, chromium is supplied as chromium chloride. A preferred embodiment of the invention comprises 50 µg chromium chloride.

Copper is a component of several enzymes associated with numerous physiological functions, including, for example, oxidase enzymes, such as cytochrome c oxidase, and cytosolic superoxide dismutase. RDA, at 224. In particular, copper is a cofactor of lysyl oxidase, which is critical for lysine cross-linking in collagen and elastin. Copper acts as an antioxidant, and promotes the synthesis of melanin and catecholamines. In addition, copper is present in the blood as ceruloplasmin which is involved in oxidizing iron prior to transport to the plasma. Copper is available in multiple forms, such as cupric oxide, copper sulfate, cupric acetate, and alkaline copper carbonate. One embodiment of the compositions and methods of the present invention comprises copper, preferably in the amount ranging from about 1.2 mg to about 1.8 mg. In a preferred embodiment of the invention, copper comprises cupric sulfate. A preferred embodiment comprises about 1.5 mg cupric sulfate.

The compositions and methods of the present invention represent a combination of essential vitamins and minerals that work together with various metabolic systems and physiological responses of the human body. The active ingredients are available from numerous commercial sources, and in several active forms or salts thereof, known to those of ordinary skill in the art. Hence, the compositions and methods of the present invention are not limited to any particular form of the vitamin or mineral ingredient described herein.

The ingredients of the present invention are preferably combined into a composition which may be in the form of a solid powder, caplets, tablets, lozenges, pills, capsules, or a liquid, and which may be administered alone or in suitable combination with other components. For example, the composition of the present invention may be administered in one or more caplets or lozenges as practical for ease of administration. Each of the vitamins and minerals is commercially available, and can be blended to form a single composition or can form multiple compositions, which may be co-administered.

To prepare the compositions of the present invention, each of the active ingredients may be combined in intimate admixture with a suitable carrier according to conventional compounding techniques. The carrier may take a wide variety of forms depending upon the form of the preparation desired for administration, e.g., oral, sublingual, nasal, topical patch, or parenteral. Preferably, the composition may consists of one to three caplets or lozenges, the composition of each being identical to each other caplet or lozenge.

In preparing the composition in oral dosage form, any of the usual media may be utilized. For liquid preparations (e.g., suspensions, elixirs, and solutions), media containing, for example water, oils, alcohols, flavoring agents, preservatives, coloring agents and the like may be used. Carriers such as starches, sugars, diluents, granulating agents, lubricants, binders, disintegrating agents and the like may be used to prepare oral solids (e.g., powders, caplets, pills, tablets, capsules, and lozenges). Controlled release forms may also be used. Because of their ease in administration, caplets, tablets, pills, and capsules represent the most advantageous oral dosage unit form, in which case solid carriers are employed. If desired, tablets may be sugar coated or enteric coated by standard techniques. All of these pharmaceutical carriers and formulations are well known to those of ordinary skill in the art. See, e.g., WADE & WALLER, HANDBOOK OF PHARMACEUTICAL EXCIPIENTS (2nd ed. 1994).

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

EXAMPLE 1

A composition of the following formulation was prepared in caplet form, including the appropriate excipients, by standard methods known to those of ordinary skill in the art:

| | |
|---|---|
| Carotenoids (Alpha-Carotene, Beta-Carotene, Cryptoxanthin, Lutein, Zeaxanthin) | 3000 IU |
| Vitamin E | 100 IU |
| Vitamin $D_3$ | 400 IU |
| Vitamin C (Ascorbic Acid) | 300 mg |
| Vitamin $B_1$ (Thiamine HCl) | 20 mg |
| Vitamin $B_2$ (Riboflavin) | 5 mg |

-continued

| | |
|---|---|
| Niacin (Niacinamide) | 25 mg |
| Folic Acid | 1 mg |
| Vitamin $B_6$ (Pyridoxine HCl) | 25 mg |
| Biotin | 100 µg |
| Pantothenic Acid (Calcium Pantothenate) | 15 mg |
| Vitamin $B_{12}$ (Cyanocobalamin) | 50 µg |
| Magnesium (Magnesium Oxide) | 50 mg |
| Manganese (Manganese Sulfate) | 1.5 mg |
| Zinc (Zinc Oxide) | 25 mg |
| Selenium (Sodium Selenate) | 100 µg |
| Chromium (Chromium Chloride) | 50 µg |
| Copper (Cupric Sulfate) | 1.5 mg |
| Alpha Lipoic Acid | 15 mg |
| Lutein | 5 mg |

EXAMPLE 2

A study is undertaken to evaluate the effectiveness of the composition of the present invention in the treatment of patients. The objective of the study is to determine whether oral intake of the composition results in an improvement of the nutritional status of the patient, either therapeutically or prophylacticly.

A double-blind, placebo controlled study is conducted over a twelve-month period. A total of sixty subjects (30 men and 30 women), aged 40 to 85 years, suffering from dietary restrictions or a disease state such as anorexia, malnutrition, gastrointestinal disorders, chronic alcoholism, chronic infections, acute infections, congestive heart failure, hyperthyroidism, poorly controlled diabetes, cheilosis, gingivitis, sensitivity to iron, hemosiderosis, hemochromatosis, or stomatitis, or a propensity or disposition to such a disease state are chosen for the study. An initial assessment of nutritional status is conducted utilizing methods such as the peroxide hemolysis test to assess vitamin E deficiency, measurement of erythrocyte transketolase activity to determine thiamine levels, determination of erythrocyte glutathione reductase activity to assess riboflavin status, and high performance liquid chromatography to directly measure PLP and pyridoxine levels.

The sixty subjects are separated into two separate groups of fifteen men and fifteen women. In the first group, each subject is administered 1 to 2 caplets, daily, of the composition as described in Example 1. In the second group (control), each subject is administered 1 to 2 placebo caplets, daily.

An assessment of nutritional status for each subject is measured at one-month intervals for a twelve month period as described above and the data is evaluated using multiple linear regression analysis and a standard students t-test. In each analysis the baseline value of the outcome variable is included in the model as a covariant. Treatment by covariant interaction effects is tested by the method outlined by Weigel & Narvaez, 12 CONTROLLED CLINICAL TRIALS 378–94 (1991). If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 16, 12, and 8 weeks, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

A statistically significant improvement in the nutritional status is preferably observed in the treated subjects upon completion of the study over the controls. The study may also look at the progression of the disease state, or the prevention or delay of a disease or disease state, or the reduction of the severity of a disease. The differences between nutritional state or the progression of the disease state, or the prevention or delay of a disease or disease state, or the reduction of the severity of a disease, between the treated subjects and controls are preferably statistically significant and or observable by clinical or other tests or evaluations. Therefore, the study confirms that oral administration of the composition of the present invention is effective as a nutritional supplement, either therapeutically or prophylacticly, for example, in preventing the severity or delaying or preventing the onset of a disease.

While there has been described what is presently believed to be the preferred embodiments of the present invention, other and further modifications and changes may be made without departing from the spirit of the invention. All further and other modifications and changes are included that come within the scope of the invention as set forth in the claims. The disclosure of all publications cited above are expressly incorporated by reference in their entireties to the same extent as if each were incorporated by reference individually.

We claim:

1. A composition for supplementing nutritional deficiencies in a patient or person in need thereof, comprising about 2400 IU to about 3600 IU carotenoids, about 80 IU to about 120 IU vitamin E, about 320 IU to about 480 IU vitamin D, about 240 mg to about 360 mg vitamin C, about 16 mg to about 24 mg thiamine, about 4 mg to about 6 mg riboflavin, about 20 mg to about 30 mg niacin, more than 0.8 mg to about 1.2 mg folic acid, about 20 mg to about 30 mg pyridoxine, about 80 µg to about 120 µg biotin, about 12 mg to about 18 mg pantothenic acid, about 40 µg to about 60 µg cobalamin, about 40 mg to about 60 mg magnesium, about 1.2 mg to about 1.8 mg manganese, about 20 mg to about 30 mg zinc, about 80 µg to about 120 µg selenium, about 40 µg to about 60 µg chromium, about 1.2 mg to about 1.8 mg copper, about 12 mg to about 18 mg alpha lipoic acid, and about 4 mg to about 6 mg lutein; wherein said composition is free of added iron.

2. The composition of claim 1, wherein said composition comprises about 3000 IU carotenoids, about 100 IU vitamin E, about 400 IU vitamin D, about 300 mg vitamin C, about 20 mg thiamine, about 5 mg riboflavin, about 25 mg niacin, about 1.0 mg folic acid, about 25 mg pyridoxine, about 100 µg biotin, about 15 mg pantothenic acid, about 50 µg cyanocobalamin, about 50 mg magnesium, about 1.5 mg manganese, about 25 mg zinc, about 100 µg selenium, about 50 µg chromium, about 1.5 mg copper, about 15 mg alpha lipoic acid, and about 5 mg lutein.

3. The composition of claim 1, wherein said composition is administered to said patient daily.

4. The composition of claim 1, wherein said composition is administered to said patient orally.

5. The composition of claim 1, wherein said composition further comprises a pharmaceutically acceptable carrier.

6. A method for supplementing nutritional deficiencies in a patient or person in need thereof, comprising administering to a patient or a person a composition comprising about 2400 IU to about 3600 IU carotenoids, about 80 IU to about 120 IU vitamin E, about 320 IU to about 480 IU vitamin D, about 240 mg to about 360 mg vitamin C, about 16 mg to about 24 mg thiamine, about 4 mg to about 6 mg riboflavin, about 20 mg to about 30 mg niacin, more than 0.8 mg to about 1.2 mg folic acid, about 20 mg to about 30 mg pyridoxine, about 80 µg to about 120 µg biotin, about 12 mg to about 18 mg pantothenic acid, about 40 µg to about 60 µg cobalamin, about 40 mg to about 60 mg magnesium, about 1.2 mg to about 1.8 mg manganese, about 20 mg to about 30 mg zinc, about 80 µg to about 120 µg selenium, about 40 µg to about 60 µg chromium, about 1.2 mg to about 1.8 mg copper, about 12 mg to about 18 mg alpha lipoic acid, and about 4 mg to about 6 mg lutein; wherein said composition is free of added iron.

7. The method of claim 6, wherein said composition comprises about 3000 IU carotenoids, about 100 IU vitamin E, about 400 IU vitamin D, about 300 mg vitamin C, about 20 mg thiamine, about 5 mg riboflavin, about 25 mg niacin, about 1.0 mg folic acid, about 25 mg pyridoxine, about 100 µg biotin, about 15 mg pantothenic acid, about 50 µg cyanocobalamin, about 50 mg magnesium, about 1.5 mg manganese, about 25 mg zinc, about 100 µg selenium, about 50 µg chromium, about 1.5 mg copper, about 15 mg alpha lipoic acid, and about 5 mg lutein.

8. The method of claim 6, wherein said composition is administered to said patient daily.

9. The method of claim 6, wherein said composition is administered to said patient orally.

10. The method of claim 6, wherein said composition further comprises a pharmaceutically acceptable carrier.

11. The composition of claim 1, wherein said nutritional deficiencies are a result of dietary restrictions.

12. The composition of claim 1, wherein said nutritional deficiencies are a result of a disease state.

13. The composition of claim 12, wherein said disease state is selected from one or more of the group consisting of anorexia, malnutrition, gastrointestinal disorders, chronic alcoholism, chronic infections, acute infections, congestive heart failure, hyperthyroidism, diabetes, cheilosis, gingivitis, hemochromatosis, hemosiderosis, and stomatitis.

14. The composition of claim 12, wherein said disease state leads to increased oxidative stress in said patient.

15. The composition of claim 12, wherein said disease state leads to elevated homocysteine levels in said patient.

16. The method of claim 6, wherein said nutritional deficiencies are a result of dietary restrictions.

17. The method of claim 6, wherein said nutritional deficiencies are a result of a disease state.

18. The method of claim 17, wherein said disease state selected from one or more of the group consisting of anorexia, malnutrition, gastrointestinal disorders, chronic alcoholism, chronic infections, acute infections, congestive heart failure, hyperthyroidism, diabetes, cheilosis, gingivitis, hemochromatosis, hemosiderosis and stomatitis.

19. The method of claim 17, wherein said disease state leads to increased oxidative stress in said patient.

20. The method of claim 17, wherein said disease state leads to elevated homocysteine levels in said patient.

21. The composition of claim 1, wherein said carotenoid comprise at least one carotenoid selected from the group consisting of alpha-carotene, beta carotene, cryptoxanthin, lutein, and zeaxanthin.

22. The composition of claim 21, wherein said carotenoid is present in the amount of about 3000 IU.

23. The composition of claim 1, wherein said vitamin E comprises d-alpha tocopheryl succinate.

24. The composition of claim 23, wherein said vitamin E is present in the amount of about 100 IU.

25. The composition of claim 1, wherein said vitamin D comprises vitamin $D_3$.

26. The composition of claim 25, wherein said vitamin is present in the amount of about 400 IU.

27. The composition of claim 1, wherein said vitamin C is in the amount of about 300 mg.

28. The composition of claim 1, wherein said thiamine comprises thiamine HCl.

29. The composition of claim 28, wherein said thiamine is present in the amount of about 20 mg.

30. The composition of claim 1, wherein said riboflavin is present in the amount of about 5 mg.

31. The composition of claim 1, wherein said niacin comprises niacinamide.

32. The composition of claim 31, wherein said niacin is present in the amount of about 25 mg.

33. The composition of claim 1, wherein said folic acid is present in the amount of about 1 mg.

34. The composition of claim 1, wherein said pyridoxine comprises pyridoxine HCl.

35. The composition of claim 34, wherein said pyridoxine is present in the amount of about 25 mg.

36. The composition of claim 1, wherein said biotin is present in the amount of about 100 µg.

37. The composition of claim 1, wherein said pantothenic acid comprises calcium pantothenate.

38. The composition of claim 37, wherein said pantothenic acid is present in the amount of about 15 mg.

39. The composition of claim 1, wherein said cobalamin comprises cyanocobalamin.

40. The composition of claim 39, wherein said cobalamin is present in the amount of about 50 µg.

41. The composition of claim 1, wherein said magnesium comprises magnesium oxide.

42. The composition of claim 41, wherein said magnesium is present in the amount of about 50 mg.

43. The composition of claim 1, wherein said manganese comprises manganese sulfate.

44. The composition of claim 43, wherein said manganese is present in the amount of about 1.5 mg.

45. The composition of claim 1, wherein said zinc comprises zinc oxide.

46. The composition of claim 45, wherein said zinc is present in the amount of about 25 mg.

47. The composition of claim 1, wherein said selenium comprises sodium selenate.

48. The composition of claim 47, wherein said selenium is present in the amount of about 100 µg.

49. The composition of claim 1, wherein said chromium comprises chromium chloride.

50. The composition of claim 49, wherein said chromium is present in the amount of about 50 µg.

51. The composition of claim 1, wherein said copper comprises cupric sulfate.

52. The composition of claim 51, wherein said copper is present in the amount of about 1.5 mg.

53. The composition of claim 1, wherein said alpha lipoic acid is present in the amount of about 15 mg.

54. The composition of claim 1, wherein said lutein is present in the amount of about 5 mg.

55. The method of claim 6, wherein said carotenoids comprise at least one carotenoid selected from the group consisting of alpha-carotene, beta-carotene, cryptoxanthin, lutein, and zeaxanthin.

56. The method of claim 55, wherein said carotenoid is present in the amount of about 3000 IU.

57. The method of claim 6, wherein said vitamin E comprises d-alpha tocopheryl succinate.

58. The method of claim 57, wherein said vitamin E is present in the amount of about 100 IU.

59. The method of claim 6, wherein said vitamin D comprises $D_3$.

60. The method of claim 59, wherein said vitamin D is present in the amount of about 400 IU.

61. The method of claim 6, wherein said vitamin C is present in the amount of about 300 mg.

62. The method of claim 6, wherein said thiamine comprises thiamine HCl.

63. The method of claim 62, wherein said thiamine is present in the amount of about 20 mg.

64. The method of claim 6, wherein said riboflavin is in the amount of about 5 mg.

65. The method of claim 6, wherein said niacin comprises niacinamide.

66. The method of claim 65, wherein said niacin is present in the amount of about 25 mg.

67. The method of claim 6, wherein said folic acid is present in the amount of about 1 mg.

68. The method of claim 6, wherein said pyridoxine comprises pyridoxine HCl.

69. The method of claim 68, wherein said pyridoxine is present in the amount of about 25 mg.

70. The method of claim 6, wherein said biotin is present in the amount of about 100 µg.

71. The method of claim 6, wherein said pantothenic acid comprises calcium pantothenate.

72. The method of claim 71, wherein said pantothenic acid is present in the amount of about 15 mg.

73. The method of claim 6, wherein said cobalamin comprises cyanocobalamin.

74. The method of claim 73, wherein said cobalamin is present in the amount of about 50 µg.

75. The method of claim 6, wherein said magnesium comprises magnesium oxide.

76. The method of claim 75, wherein said magnesium is present in the amount of about 50 mg.

77. The method of claim 6, wherein said manganese comprises manganese sulfate.

78. The method of claim 77, wherein said manganese is present in the amount of about 1.5 mg.

79. The method of claim 6, wherein said zinc comprises zinc oxide.

80. The method of claim 79, wherein said zinc is present in the amount of about 25 mg.

81. The method of claim 6, wherein said selenium comprises sodium selenate.

82. The method of claim 81, wherein said selenium is present in the amount of about 100 µg.

83. The method of claim 6, wherein said chromium comprises chromium chloride.

84. The method of claim 83, wherein said chromium is present in the amount of about 50 µg.

* * * * *